United States Patent [19] [11] Patent Number: 5,866,747
Barger [45] Date of Patent: Feb. 2, 1999

[54] ALKYLATION OF ALKANES WITH MIXTURES OF ALKENES AND ALKYL HALIDES

[75] Inventor: Paul T. Barger, Arlington Heights, Ill.

[73] Assignee: UOP LLC, Des Plaines, Ill.

[21] Appl. No.: 867,639

[22] Filed: Jun. 2, 1997

Related U.S. Application Data

[63] Continuation-in-part of Ser. No. 363,068, Dec. 23, 1994, abandoned.

[51] Int. Cl.[6] .................................................. C07C 2/56
[52] U.S. Cl. ......................... 585/711; 585/726; 585/728; 585/729
[58] Field of Search ................................. 585/728, 729, 585/726, 711

[56] References Cited

U.S. PATENT DOCUMENTS

| | | | |
|---|---|---|---|
| 2,882,324 | 4/1959 | Schmerling | 260/666 |
| 2,999,074 | 9/1961 | Bloch et al. | 252/442 |
| 3,585,252 | 6/1971 | Kennedy | 260/676 |
| 3,800,001 | 3/1974 | Prescott et al. | 585/728 |
| 3,976,714 | 8/1976 | Rodewald | 260/683.47 |
| 4,229,611 | 10/1980 | Kramer | 585/728 |
| 4,579,996 | 4/1986 | Freide et al. | 585/642 |

FOREIGN PATENT DOCUMENTS 0535142  3/1941  United Kingdom .

*Primary Examiner*—Glenn Caldarola
*Assistant Examiner*—In Suk Bullock
*Attorney, Agent, or Firm*—Thomas K. McBride; Frank S. Molinaro

[57] ABSTRACT

Although alkenes commonly are used to alkylate alkanes using various solid acid catalysts, the process is severely hampered by short catalyst lifetimes attending substantial alkene oligomerization. This problem can be avoided by using an alkene-alkyl chloride mixture as the alkylating agent. Thus, alkylation of isobutane by a butyl chloride/butene mixture at a molar ratio of 1:3 in the presence of an $AlCl_3$-type Friedel-Crafts catalyst at 30° C. maintains at least an 80% conversion of (alkene and alkyl chloride) for almost twice as long as is the case for a 1:19 molar ratio of butyl chloride/butene.

16 Claims, 1 Drawing Sheet

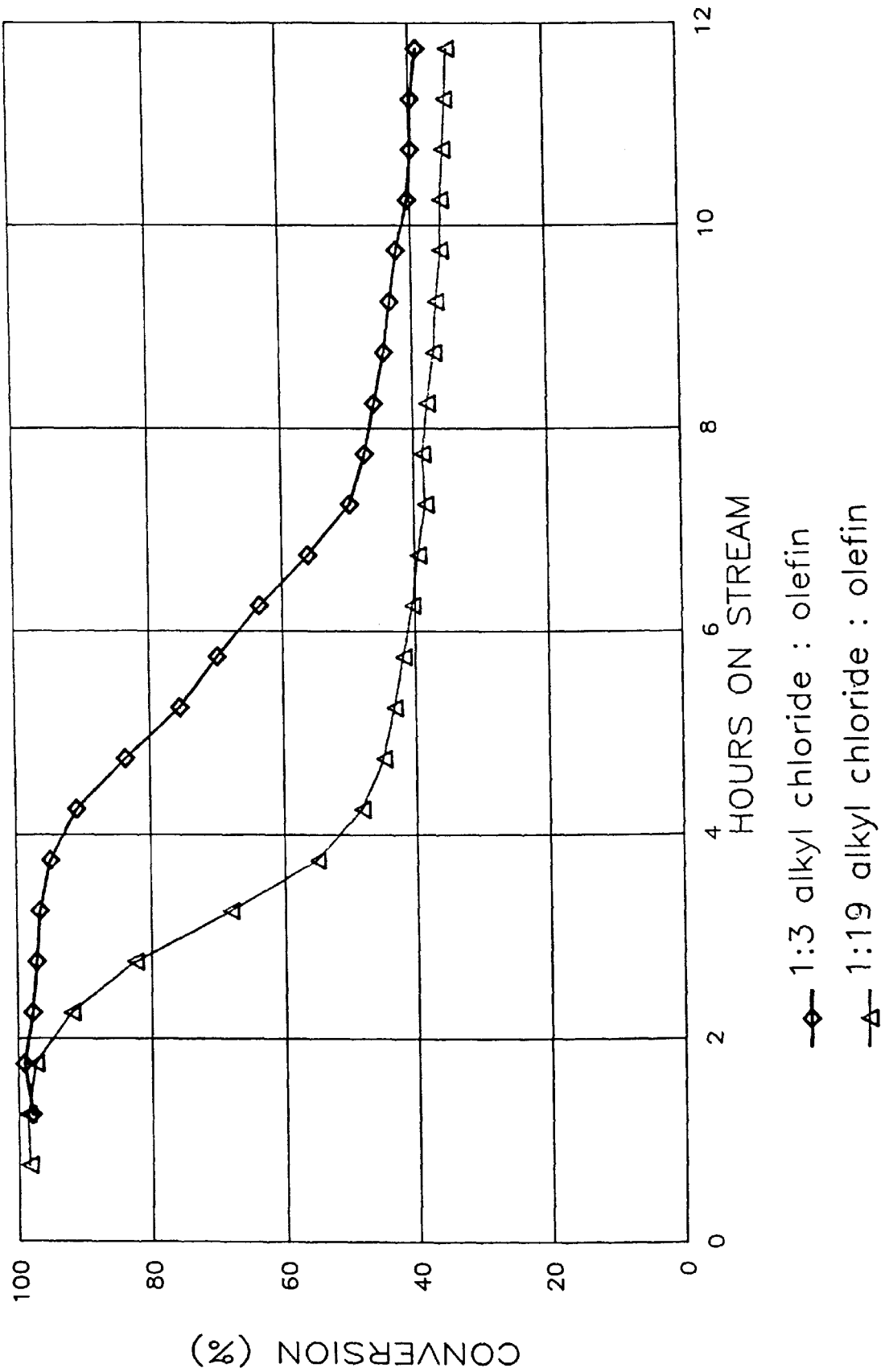

ALKYLATION OF ALKANES WITH MIXTURES OF ALKENES AND ALKYL HALIDES

CROSS REFERENCE TO RELATED APPLICATION

This application is a continuation-in-part of my application, Ser. No. 08/363,068, filed Dec. 23, 1994, now abandoned, all of which is incorporated hereby.

FIELD OF THE INVENTION

This invention relates to the alkylation of lower alkanes with a mixture of lower alkenes and lower alkyl halides to afford other alkanes, principally in the C5–C12 range, suitable for use as a motor fuel.

BACKGROUND OF THE INVENTION

Even in the era of anti-knock additives such as tetraethyl lead, the use of alkylate as a component in motor fuel gained both universal acceptance and importance. In the ensuing years alkylate has become an even more important component of motor fuel. Alkylate is an economical, clean-burning, high-octane, low volatility product that is becoming increasingly important as the composition of gasoline changes in response to environmental concerns and legislation. The governmental regulations most applicable to the increasing importance of alkylates are those affecting lead and butane. Adding lead anti-knock compounds was the easiest way to raise gasoline octane, but because of continuing concerns over the effects of lead emissions the phasing out of lead in gasoline was required, a process over 90% complete. Butane is another effective octane-booster but tends to evaporate from gasoline, especially in warm weather, contributing to smog formation. Recent EPA regulations have effected their virtually complete removal from gasoline.

The term "alkylate" generally refers to a complex mixture resulting from the alkylation of C2–C6 alkenes (olefins) present or formed in a feedstream with intermediates arising primarily from alkanes, especially branched alkanes, and predominantly those with 4 carbon atoms, especially isobutane, also present in the same feedstream. It is most desirable that the complex product mixture from C4 alkenes and alkanes, referred to as alkylate, contains predominantly trimethylpentanes, since these are high-octane components which add considerable value to motor fuel, yet the chemistry of alkylation affords a dazzling variety of products resulting from only a few basic chemical reactions characteristic of the carbocations, the species which plays a central role in the alkylation process. Thus, chemical processes as chain transfer (intermolecular hydride transfer and alkyl shifts), oligomerization and disproportionation serve to place into the alkylate, as byproduct, materials of from 5–12+ carbon atoms from a feed containing only C4 alkenes and C4 alkanes.

The alkylation of alkenes is catalyzed by strong acids generally. Although such alkylation has been the focus of intense and continuing scrutiny for several decades, the requirements of optimum selectivity while achieving high conversion have heretofore narrowed, for all practical purposes, the commercial choice of catalyst to sulfuric acid and liquid hydrogen fluoride. While processes based on each of these acids have gained commercial acceptance those based on HF have been favored at least in part because of the relative ease of HF regeneration. A brief but valuable overview of HF-catalyzed alkylation is presented by B. R. Shah in "Handbook of Petroleum Refining Processes", R. A. Meyers, editor, McGraw-Hill Book Company, 1986, pp 1–3 through 1–28.

In a rather over-simplified description, the HF-catalyzed alkylation process is carried out as follows. Alkene and isobutane feedstocks are combined and mixed with HF in an alkylation reaction zone. The reactor effluent is separated into the desired alkylate, acid, and other light gases which are predominantly unreacted isobutanes. The HF is either recycled to the reactor directly or regenerated, in whole or in part, prior to its being recycled to the reactor. Unreacted isobutane also is recycled to the reactor, and the alkylate is then used in motor fuel blending.

Recently HF (hydrofluoric acid) has come under environmental pressure. Hydrofluoric acid is classified as an Acutely Hazardous Material, and in Southern Calif. the Board of the South Coast Air Quality Management District recently required that the use of HF in alkylation be phased out by Jan. 1, 1998. Consequently there is increasing reason to seek substitutes for HF as an alkylation catalyst for alkylate production. It is quite desirable to have a solid acid as an effective catalyst, for this permits development of fixed bed processes, a desirable alternative in the petroleum refining industry.

In response to environmental sensitivity to hydrogen fluoride a spate of solid acid catalysts has been suggested as alternative alkylation catalysts, especially Lewis acids such as aluminum halides, boron trifluorides, antimony pentafluoride, and so forth and modified or supported Bronsted acids such as sulfated zirconia. In all processes heretofore suggested the solid acid alkylation catalysts have been used in conjunction with alkenes. Although traditional and conventional alkylation to form alkylate of interest as a motor fuel employs the reaction between alkanes and alkenes, such alkylation processes are encumbered by serious disadvantages when solid acids are used as the catalyst. In particular, the foregoing alkylation process always is accompanied by oligomerization of alkenes, which also is an acid-catalyzed reaction, and the relative amount of oligomerization increases radically when a solid acid is used as the alkylation catalyst relative to the use of, for example, HF as the alkylation catalyst. The traditional alkylation process catalyzed by a solid acid catalyst also is plagued by limited stability of the catalyst; lifetimes under about 6 hours are common.

Thus there are two problems to be overcome in solid bed alkylation process using an alkane-alkene mixture; oligomerization of the alkene and a short catalyst lifetime. One solution to this problem is to conduct alkylation at a very high alkane to alkene ratio, say 100:1. However, such a high ratio is impractical because it requires a very large recycle stream and because of the increased reactor size required for a given productivity (e.g., as measured by alkylate formed per hour). We conjectured that substitution of an alkene by an alkyl halide might provide results equivalent to a very high alkane/alkene ratio. In fact our speculations proved correct. Equally important is our observation that only a partial substitution of an alkene by an alkyl halide also provides substantial benefits. The resulting process of alkylation using an alkane and an alkene-alkyl halide mixture in the presence of a solid acid catalyst is accompanied by substantially lower oligomerization and, even more importantly, substantially increased catalyst stability as measured by catalyst life.

There appears to be little relevant to our discovery in the prior art. U.S. Pat. No. 3,585,252 describes the preparation of alkylate by coupling alkyl halides with organoaluminum compounds, especially trialkylaluminum compounds. In U.S. 4,229,611 the patentee describes the use of a strong Lewis acid system to catalyze the alkylation reaction between alkyl halides and alkenes. The use of clays to convert C1–C4 monohaloalkanes into hydrocarbons of a higher carbon number than the individual reactants is described in U.S. 4,579,996. The clays used contain hydrogen ions and/or metal cations introduced by exchange or deposition, and the use of pillared layered clays is preferred. Finally, GB 545,142 teaches alkylation of, e.g., isobutane with highly oligomerized olefins which are depolymerized by HCl, introduced either per se or via use of an alkyl halide as an activating agent whose sole function is to provide the requisite HCl as a result of its dehydrohalogenation under reaction conditions. Note that the patentee requires the use of an oligomerized alkene, thus perforce fails to recognize the detrimental effect of such oligomers on catalyst life, and also fails to recognize the use of alkyl halides as alkylating agents for the alkylation of alkanes. We note that an explicit requirement of our invention which is a logical consequence of the detrimental effect of olefin polymers - is that the feedstock be substantially free of polymeric alkenes.

Although the prior art practices alkylation of alkanes with alkenes in the presence of halides, the latter generally are present on the order of 1000 ppm, which corresponds to a molar ratio of halide to olefin of about 0.05. However, no one previously has recognized an incremental benefit resulting from the use of the substantially higher halide levels practiced in this invention.

SUMMARY OF THE INVENTION

The purpose of this invention is the preparation of alkylate in the C5–C12+ range, suitable as a motor fuel, by alkylation of alkanes. An embodiment is the reaction of a mixture of alkenes and alkyl halides with alkanes in the presence of a solid acid catalyst. In a more specific embodiment the alkyl halides and alkenes contain between 3 and about 5 carbon atoms and the alkanes contain from about 4 up to about 6 carbon atoms. In a still more specific embodiment the alkanes are branched alkanes. In another specific embodiment the alkyl halides are secondary or tertiary alkyl halides. In yet another specific embodiment the alkyl halide is sec-butyl chloride or tert-butyl chloride, the alkene is a butene, and the alkane is isobutane. In still another embodiment the molar ratio of alkyl chloride to alkene is between 1:5 and 9:1.

DESCRIPTION OF THE FIGURE

FIG. 1 graphically portrays catalyst deactivation in the alkylation of isobutane at 30° C. using as the alkylating agent a) alkene in the presence of a minor amount of sec-butyl chloride and b) an alkyl chloride/alkene mixture in a molar ratio of 1:3.

DESCRIPTION OF THE INVENTION

We have found that the dual problems of alkene oligomerization and catalyst instability attending the conventional alkylation process of alkenes by alkanes using solid acid catalysts can be circumvented using a modified process where the alkene reactants are replaced by a mixture of alkenes and alkyl halides. Our process is operable with a multitude of solid acid catalysts; the process is relatively independent of the particular solid acid catalyst employed except for the attending reaction conditions. Instead the nub of our invention is the reaction effecting alkylation using a mixture of alkenes and alkyl halides as a replacement for alkenes. The result is a process where catalyst lifetimes are increased substantially and where the product alkylate is otherwise largely comparable to that produced in a conventional process.

The alkanes which may be used in the practice of our invention contain from 4 to 6 carbon atoms and the branched alkanes are particularly useful in the practice of our invention. Suitable alkanes are illustrated by n-butane, 2-methylpropane (commonly called isobutane), 2-methylbutane (or isopentane), 2,2-dimethylpropane (neopentane), n-pentane, n-hexane, 2,3-dimethylbutane, 2-methylpentane, 3-methylpentane, and 2,2-dimethylbutane.

The alkenes which are used in the practice of our invention contain from 2 to 6 carbon atoms and are ethylene, propylene, the butenes, the pentenes, and the hexenes.

The alkyl halides which are employed in the practice of our invention have from 3 up to about 5 carbon atoms. This is not to imply that higher alkyl halides are unreactive, but rather that the resulting alkylate is most useful as a motor fuel when the alkyl halide is in the designated carbon range. The chlorides and bromides are the most important of the alkyl halides in the practice of our invention, and alkyl chlorides are most important of all. Among the alkyl halides which may be used in the practice of this invention, as exemplified by the chlorides, are 1-chloropropane, 2-chloropropane, 1-chlorobutane, 2-chlorobutane, 1-chloro-2-methylpropane, 2-chloro-2-methylpropane, 1-chloropentane, 2-chloropentane, 3-chloropentane, 1-chloro-3-methylbutane, 2-chloro-3-methylbutane, 1-chloro-2-methylbutane, 2-chloro-2-methylbutane, and 1-chloro-2,2-dimethylpropane. Among the alkyl halides the secondary and tertiary alkyl halides are favored in the practice of this invention. Such halides, exemplified as their chlorides, are represented by 2-chloropropane, 2-chloro-2-methylpropane, 2-chlorobutane, 2-chloropentane, 3-chloropentane, 2-chloro-2-methylbutane, and 2-chloro-3-methylbutane.

The feedstock of our invention is a mixture of one or more alkanes, alkenes, and alkyl halides. The molar ratio of alkane to (alkene plus alkyl halide) may be as high as 1 00:1 and as low as 1:1, although the range between 20:1 through 5:1 is much more usual. The molar ratio of alkyl halide to alkene is in the range from about 1:5 up to about 9:1. Although an alkyl halide may be used as a total replacement of an alkene, such total replacement is not the subject of this invention. It is preferred that the alkyl halide/alkene molar ratio be at least about 1:3. The sole additional qualification of the feedstock, which is a consequence of our discovery that catalyst life is adversely affected by oligomeric alkenes, is that it be substantially free of polymeric (oligomeric) alkenes, by which is meant that the feedstock is to contain less than about 1 weight percent polymeric alkenes. Most preferably the feedstock will contain no more than about 0.2 weight percent polymeric alkenes.

The reaction between alkanes and an alkene-alkyl chloride mixture to form alkylate is catalyzed by solid acid catalysts. Generally effective catalysts for use in our invention are solid acid catalysts identified as strong Lewis acids as well as supported sulfuric and phosphoric acids. Examples of such materials include silica impregnated with sulfuric acid (U.S. Pat. No. 5, 336,833), heteropoly acids, as exemplified by heteropolymolybdates and heteropolytungstates, especially as supported on molecular sieves (U.S. Pat. No. 5,324,881 for examples of heteropoly acids as well as supports), sulfated zirconia as exemplified in U.S. 5,310,868, various zeolitic materials as summarized in U.S. Pat. No. 5,258,569, supported fluorinated sulfonic acids (U.S. Pat. No. 5,245,100), Lewis acids such as $BF_3$, $SbF_5$, $AlCl_3$, $GaCl_3$, and so forth (U.S. Pat. No. 5,245,101; 5,190,904; 5,157,197) either alone or in combination with zeolitic materials (U.S. Pat. No. 5,191,148) or as composites. The Lewis acids based on aluminum, gallium, antimony and boron halides are especially attractive. It needs to be emphasized that the foregoing named materials are only exemplary, and not intended to be exhaustive, of the solid acid catalysts which may be employed in the practice of our invention.

Catalytic composites which are particularly preferred comprise a refractory inorganic oxide, the reaction product of a first metal halide and bound surface hydroxyl groups of the refractory inorganic oxide, a second metal cation, and optionally a zerovalent third metal, where the refractory inorganic oxide is selected from the group consisting of alumina, titania, zirconia, chromia, silica, boria, silica-alumina, aluminum phosphate, and combinations thereof, said first metal halide is a fluoride, chloride, or bromide and the first metal is selected from the group consisting of aluminum, zirconium, tin, tantalum, titanium, gallium, antimony and boron, and the second metal cation is a monovalent metal cation, especially alkali metal cations, or alkaline earth metal cations. The third metal is selected from the group consisting of platinum, palladium, nickel, ruthenium, rhodium, osmium and iridium, as well as combinations thereof, and is present optionally. The analogs of our catalyst without the metal cations are well known in the art (U.S. Pat. No. 2,999,074 and 3,318,820) and the extensive description of their preparation is applicable here with the exception of impregnation with a monovalent cation or alkaline earth metal cation. The following description then will suffice merely to afford the reader an understanding of our preferred catalytic composite.

The refractory inorganic oxides suitable for use in the preferred composites of this invention have a surface area of at least about 35 $m^2$/g, preferably greater than about 50 $m^2$/g, and more desirably greater than 100 $m^2$/g. There appears to be some advantage to working with materials having as high a surface area as possible, although exceptions are known which preclude making this a general statement. Suitable refractory inorganic oxides include alumina, titania, zirconia, chromia, silica, boria, silica-alumina, aluminum phosphate, and combinations thereof. Of these alumina is particularly preferred. Any alumina phase may be used so long as it has a surface area of at least 35 $m^2$/g and has surface hydroxyl groups, which for all practical matters excludes alpha-alumina. Among the phases which may be used are included gamma-, etc-, and theta-alumina, although the various phases are not necessarily equivalent in their effectiveness as a motor fuel alkylation catalyst. Aluminum phosphate is another favored refractory material.

It is required that the refractory inorganic oxide have bound surface hydroxyl groups, by which is meant not adsorbed water but rather hydroxyl (OH) groups whose oxygen is bound to the metal of the inorganic oxide. These latter hydroxyl groups sometimes have been referred to as chemically combined hydroxyl. Since the presence of adsorbed water is generally detrimental to the preparation of the catalysts of our invention, the refractory inorganic oxides are first treated to remove surface hydroxyl groups arising from water, most usually by calcination at a temperature which specifically and preferentially removes physically adsorbed water without chemically altering the other hydroxyl groups. For example, calcination temperatures ranging from about 350° C. to about 700° C. are usually satisfactory where the inorganic oxide is alumina.

The catalytic composites optionally contain a metal having hydrogenation activity. Where a hydrogenation-active metal is present it generally is deposited on the refractory inorganic oxide prior to the reaction of its bound surface hydroxyl groups with metal halides. Although such a procedure has proven both convenient and effective, we do not wish to imply that this is the only sequence which may be used to afford an effective catalyst. Metals which have been found to be particularly effective include nickel and the noble metals of platinum, palladium, ruthenium, rhodium, osmium, and iridium, although platinum and palladium are by far the most desirable of the noble metals. The desired metal may be composited with the refractory inorganic oxide in any desired manner, such as by impregnation, coprecipitation, dipping, and so forth, of a suitable salt followed by reduction of the metal to its zerovalent state. Such methods are well known and need not be described here. Hydrogenation-active metal levels may range between about 0.01 up to about 1.0 weight percent for the noble metals, based on the weight of the finished catalyst, and from about 0.1 up to about 5 weight percent for nickel. The composite of the metal and refractory inorganic oxide is dried and calined under controlled conditions to remove physically adsorbed water but under sufficiently mild conditions so that the "chemically combined" hydroxyl groups are not eliminated.

The more usual way of introducing a hydrogenation-active metal into the catalytic composites of our invention is by coimpregnation of the refractory inorganic oxide with a salt of the hydrogenation-active metal together with one or more monovalent or alkaline earth metal cations of our invention. But as stated above it is not believed that the particular procedure or sequence used is determinative of success of, or even of substantial significance to, the final catalytic composite.

The next stage in the preparation of our catalytic composites, whether or not a metal with hydrogenation activity has been deposited thereon, is to deposit on the composite one or more monovalent metal or alkaline earth metal cations. Such metals include lithium, sodium, potassium, cesium, rubidium, silver, copper(1), beryllium, magnesium, calcium, strontium, and barium. Among the monovalent metal cations the alkali metal cations are favored. The amount of metal cation which is impregnated on the composite is an amount having a gram atom equivalent from about 0.1 up to about 2 weight percent potassium, which is 0.0026 gram atoms potassium up to 0.051 gram atoms per 100 gram support. We define a "gram atom equivalent" of another metal cation as being a number of gram atoms of the metal divided by its valence per 100 grams support. For example, for magnesium the gram atom equivalent is 0.0013 up to about 0.0255 gram atoms per 100 gram support, which is equal to 0.031 up to about 0.62 weight percent.

Impregnation of the composite by the monovalent metal or alkaline earth metal cation may be done simply by mixing the composite with a suitable aqueous solution of the salt and removing water. The particular monovalent or alkaline earth metal salt used is not especially important so long as it provides sufficient solubility in water. As a practical matter, the halides, nitrates, and acetates may be the most commonly employed salts. Salts prone to precipitation should be avoided in order to avoid non-uniform impregnation, but otherwise there are no serious limitations on the salts which may be used. After evaporation of excess water, materials generally are dried at a temperature between about 100° and 200° C. for 2–4 hours and then calcined at a temperature which specifically and preferentially removes physically adsorbed water without chemically altering the other hydroxyl groups. As mentioned before, temperatures ranging from about 350° C. to about 700° C. usually are satisfactory where the inorganic oxide is alumina.

Subsequent to metal deposition and calcination, the bound surface hydroxyl groups of the refractory inorganic oxide are reacted with a metal halide having Friedel-Crafts activity. Among the metals which may be used are included aluminum, zirconium, tin, tantalum, titanium, gallium, antimony, and boron. Suitable halides are the fluorides, chlorides, and bromides. Representative of such metal halides include aluminum chloride, aluminum bromide, ferric chloride, ferric bromide, zirconium chloride, zirconium bromide, boron trifluoride, titanium tetrachloride, gallium chloride, tin tetrachloride, antimony fluoride, tantalum chloride, tantalum fluoride, and so forth. Of these metal halides the aluminum halides are preferred, especially aluminum chloride. Except for boron trifluoride, the chlorides are generally the preferable halides.

The reaction between the metal halides of this invention and the bound surface hydroxyl groups of the refractory inorganic oxide is readily accomplished by, for example, sublimation or distillation of the metal halide onto the surface of the particles of the metal inorganic oxide composite. The reaction is attended by the elimination of between about 0.5 and 2.0 moles of hydrogen halide per mole of metal halide adsorbed thereon. The reaction temperature will depend upon such variables as the reactivity of the metal halides and its sublimation temperature or boiling point, where the metal halide is reacted in the gas phase, as well as on the nature of the refractory inorganic oxide. For example, using aluminum chloride and alumina as our specific examples reaction readily occurs within the range between about 190° through 600° C.

The amount of metal halide which is reacted with the bound surface hydroxyl groups of the refractory inorganic oxide is generally given in terms of the weight percent of the Friedel-Crafts metal on the composite. This amount will vary with the refractory inorganic oxide used, the relative number of bound surface hydroxyls of the inorganic oxide (which may be related to the particular oxide phase utilized), the specific Friedel-Crafts metal halide employed, as well as the particular procedure used to effect reaction between the Friedel-Crafts type metal halide and the bound surface hydroxyl. As a rough rule of thumb for aluminum chloride on alumina, as an example, the amount of aluminum chloride reacted expressed as weight percent aluminum in the final composite ranges from about 0.1 up to about 2.5%, with the level being a function primarily of the number of bound surface hydroxyl groups on the refractory inorganic oxide.

The reaction conditions for effecting alkylation clearly will depend upon the alkane and alkene-alkyl chloride mixture used as well as the particular catalyst employed. Sufficient pressure is used to ensure a liquid phase reaction, but the pressure is otherwise unimportant as a reaction variable influencing the course of alkylation. Clearly the pressure necessary to maintain a liquid phase reaction depends upon the reaction temperature as well as the reactants, but pressures in the range of 100–1500 psig generally will suffice. Reaction temperatures may be as low as about −40° C. and as high as about 150° C., depending upon the reactants as well as the particular solid acid catalyst used. For example, for the preferred catalyst described above temperatures between about 10° and about 50° C. generally will suffice and are preferred.

As alluded to above, the alkylation reaction is performed as a continuous reaction in the liquid phase. The catalytic composite generally is present as a fixed bed although this is not a necessary limitation but rather merely represents a convenient reaction mode. A feedstock containing a mixture of alkenes having from 2 up to about 6 carbon atoms, alkyl chlorides having from 3 up through about 5 carbon atoms and alkanes having from 4 up through about 6 carbon atoms is passed in the liquid phase over the catalyst maintained at a temperature between about −10° and about 150° C. The reaction may be run in either an upflow or a downflow mode and the mode selected is a matter of choice. The feedstock generally is passed over the catalyst at a liquid hourly space velocity between about 0.5 and about 5.0 $hr^{-1}$ based on total feed.

The following examples are merely illustrative of our invention and are not intended to limit it in any way.

EXAMPLE 1

Alkylation with 1:3 Butyl Chloride:Butene Feedstock. A catalyst (16.4 g) prepared by subliming $AlCl_3$ onto a support consisting of 0.25 weight percent Pt and 5.0 weight percent K on a spherical (1/32 inch diameter) gamma alumina base was loaded into a 7/8" ID stainless steel reactor under a $N_2$ stream to avoid any contact with moisture. The catalyst was pretreated with $H_2$ at 350° C. for 6 hours, then cooled to 30° C. and flushed with liquid isobutane containing 1000 ppm chloride as sec-butyl chloride at 450 psig, 97 g/hr for 2 hours. After completion of the flush, an isobutane/2-butene/i-butene/sec-butyl chloride/tert-butyl chloride feedstock with a molar ratio of 25/0.56/0.19/0.19/0.06 (1:3 alkyl chloride:olefin molar ration) was cut into the plant at 90 g/hr while maintaining the temperature and pressure. This feed was maintained for 12 hours. FIG. 1 shows that the conversion fell from greater than 97% to 80% over about 5 hours. From 2.3 to 1.8 g of $C_{5+}$ products were recovered per gram of butene equivalent (i.e., the butene plus the amount of sec-butyl chloride containing as many moles as 1 g butene) converted during this period indicating that paraffin alkylation was predominant.

EXAMPLE 2

Alkylation with 1:19 Butyl Chloride:Butene Feedstock. The same catalyst as in Example 1 was pretreated with $H_2$ and flushed with isobutane using the same procedure. After completion of the flush an isobutane/2-butene/i-butene/sec-butyl chloride/tert-butyl chloride feed with a molar ratio of 25/0.71/0.24/0.04/0.01 (1:19 butyl chloride:olefin molar ratio) was cut into the plant and maintained for 12 hours. FIG. 1 shows that conversion fell from about 99% to 80% over about 2.5 hours. The gram of $C_{5+}$ products produced per gram of butene converted dropped from 2.1 to 1.5 over this time indicating that olefin oligomerization was increasing as the catalyst deactivated.

These examples demonstrate the substantial benefit in catalyst stability that is obtained in paraffin alkylation by the use of an alkylchloride/olefin feed with a molar ratio of 1:5 or higher as opposed to a feed consisting of an olefin with only trace levels of alkylchloride. In addition, in the case of an alkylchloride feed the observed products appear to arise predominantly from the desired paraffin alkylation reaction, whereas olefin oligomerization appears to become significant in the case of an olefin feed, particularly at lower conversion levels.

What is claimed is:

1. A process for the preparation of alkylate comprising reacting in the liquid phase in the presence of a solid acid catalyst under reaction conditions a mixture of an alkene containing from 2 up to about 6 carbon atoms, said mixture being substantially free of polymeric alkenes, and an alkyl halide containing from 3 up to about 5 carbon atoms with an alkane having from 4 up to about 6 carbon atoms to form as the product an alkylate containing alkanes having a greater number of carbon atoms than either reactant, where said mixture has a molar ratio of alkyl halide to alkene from about 1:5 up to about 9:1.

2. The process of claim 1 where the alkyl halide is a butyl halide and the olefin is a butene.

3. The process of claim 2 where the butyl halide is a secondary or tertiary butyl halide.

4. The process of claim 1 where the alkyl halide is a secondary or tertiary alkyl halide.

5. The process of claim 1 where the halide is a chloride or a bromide.

6. The process of claim 1 where the alkane is a butane.

7. The process of claim 6 where the butane is isobutane.

8. The process of claim 1 where the molar ratio of alkane to the mixture of alkene and alkyl halide is from about 10 to about 30.

9. The process of claim 1 where the solid acid catalyst is selected from the group consisting of aluminum halides, gallium halides, boron halides, and antimony halides.

10. The process of claim 1 where the alkyl halide is sec-butyl chloride or tert-butyl chloride, the alkene is butene-2, and the alkane is isobutane.

11. The process of claim 1 where the alkane is a branched alkane.

12. The process of claim 1 where reaction conditions include a temperature from about 40° up to about 150° C.

13. The process of claim 1 where the molar ratio of alkyl chloride to alkene is at least 1:3.

14. The process of claim 1 where said mixture contains less than about 1 weight percent polymeric alkenes.

15. The process of claim 14 where said mixture contains less than about 0.2 weight percent polymeric alkenes.

16. A process for the preparation of alkylate comprising reacting in the liquid phase in the presence of a solid acid catalyst under reaction conditions a mixture of an alkene selected from the group consisting of propylene, butenes, pentenes, and hexenes, said mixture being substantially free of polymeric alkenes, and an alkyl halide containing from 3 up to about 5 carbon atoms with an alkane having from 4 up to about 6 carbon atoms to form as the product an alkylate containing alkanes having a greater number of carbon atoms than either reactant, where said mixture has a molar ratio of alkyl halide to alkene from about 1:5 up to about 9:1.

* * * * *